(12) United States Patent
Laufer et al.

(10) Patent No.: US 9,199,925 B2
(45) Date of Patent: Dec. 1, 2015

(54) CARBODIIMIDES FROM TRISUBSTITUTED AROMATIC ISOCYANATES, A METHOD FOR PRODUCING SAME, AND THE USE OF SAME

(75) Inventors: Wilhelm Laufer, Ellerstadt (DE); Benjamin Bechem, Mannheim (DE); Armin Eckert, Oberhausen (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 177 days.

(21) Appl. No.: 14/115,487

(22) PCT Filed: Apr. 27, 2012

(86) PCT No.: PCT/EP2012/057708
§ 371 (c)(1),
(2), (4) Date: Jan. 14, 2014

(87) PCT Pub. No.: WO2012/150181
PCT Pub. Date: Nov. 8, 2012

(65) Prior Publication Data
US 2014/0121412 A1    May 1, 2014

(30) Foreign Application Priority Data

May 5, 2011  (EP) ..................................... 11164899
Nov. 9, 2011  (EP) ..................................... 11188364

(51) Int. Cl.
*C07C 267/00* (2006.01)
*C08G 18/02* (2006.01)
*C08K 5/29* (2006.01)

(52) U.S. Cl.
CPC ............ *C07C 267/00* (2013.01); *C08G 18/025* (2013.01); *C08K 5/29* (2013.01)

(58) Field of Classification Search
None
See application file for complete search history.

(56) References Cited

U.S. PATENT DOCUMENTS

| | | |
|---|---|---|
| 3,193,522 A | 7/1965 | Neumann et al. |
| 3,711,439 A | 1/1973 | Loew |
| 3,776,882 A | 12/1973 | Witzler et al. |
| 5,130,360 A | 7/1992 | Ulrich |
| 5,498,356 A | 3/1996 | Kamakura et al. |
| 5,859,166 A | 1/1999 | Sasaki et al. |

FOREIGN PATENT DOCUMENTS

DE    1130594 B    5/1962

OTHER PUBLICATIONS

International Search Report from International Application No. PCT/EP2012/057708, May 29, 2012, two pages.
Wagner, K. et al., "Diisocyanatocarbodiimides,—Polycarbodiimides, and Their Derivatives", Angew. Chem. Int. Ed. Engl. 20, (1981), pp. 819-830, Verlag Chemie Gmbh, Weinheim, Germany.
Rahman, A. K. et al., "Catalytic conversion of isocyanates to carbodiimides by cyclopentadienyl manganese tricarbonyl and cyclopentadienyl iron dicarbonyl dimer", Tetrahederon Letters 48 (2007) pp. 6002-6004, Elsevier, Amsterdam, The Netherlands.

*Primary Examiner* — Rosalynd Keys
*Assistant Examiner* — Jennifer C Sawyer

(57) ABSTRACT

The invention relates to innovative carbodiimides, to a process for preparing them and to the use thereof as stabilizer, crosslinker and/or compatibilizer in thermoplastics, ester-based polyols for polyurethane applications, in rigid foam, in flexible foam or, for example, in CASE (Coatings Adhesives Sealants Elastomers) applications.

14 Claims, No Drawings

CARBODIIMIDES FROM TRISUBSTITUTED AROMATIC ISOCYANATES, A METHOD FOR PRODUCING SAME, AND THE USE OF SAME

The invention relates to innovative carbodiimides, to a process for preparing them and to the use thereof as stabilizer, crosslinker and/or compatibilizer in thermoplastics, ester-based polyols for polyurethane applications, in rigid foam, in flexible foam or, for example, in CASE (Coatings Adhesives Sealants Elastomers) applications.

Carbodiimides have become established in numerous applications for example, as antihydrolysis agents for thermoplastics, polyols, polyurethanes, etc.

For these purposes the use of sterically hindered carbodiimides is preferred. Known in particular in this context are bis-2,6-diisopropylphenyl carbodiimide and/or carbodiimides based on 2,4,6-triisopropylphenyl 1,3-diisocyanate or based on tetramethylxylylene diisocyanate, available from Rhein Chemie Rheinau GmbH. The carbodiimides known in the prior art, however, have the disadvantages in certain applications, as for example in the production of films at relatively high temperatures, of being volatile or thermally unstable, and they may give off volatile toxic compounds and/or must in general, owing to the relatively low functionality, be added uneconomically in high quantities.

There is therefore a demand for carbodiimides which do not exhibit the aforementioned disadvantages.

An object of the present invention was therefore the provision of carbodiimides which are preparable temperature-stably and economically.

Surprisingly it has been possible to achieve this object by means of particular carbodiimides.

The present invention accordingly provides carbodiimides of the formula (I)

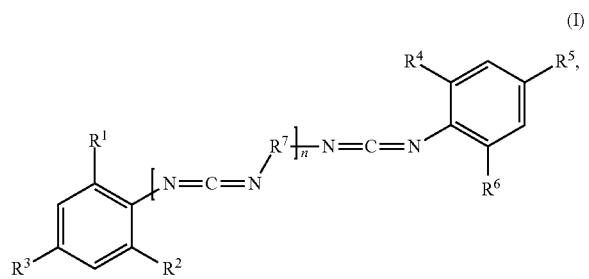

(I)

in which $R^1$, $R^2$, $R^3$, $R^4$, $R^5$, and $R^6$ independently of one another are each $C_1$-$C_{20}$-alkyl, $C_3$-$C_{20}$-cycloalkyl, $C_6$-$C_{15}$-aryl and/or $C_7$-$C_{15}$-aralkyl, $R^7$ is $C_1$-$C_{18}$-alkylene, $C_5$-$C_{18}$-cycloalkylene, alkyl-substituted arylene and/or $C_7$-$C_{18}$-aralkylene, preferably alkyl-substituted arylene and/or $C_7$-$C_{18}$-aralkylene, and n is an integer from 1 to 500.

Preferably n is between 1 and 50, very preferably 4-50.

In one embodiment of the invention it is also possible for mixtures of the compounds of the formula (I) to occur. In the case of the mixture, it is also possible for fractional numbers to arise when the average for n is determined.

The alkyl-substituted arylene is preferably $C_1$-$C_4$-alkyl-substituted arylene, more preferably singly to triply substituted $C_1$-$C_4$-alkyl-substituted arylene, very preferably triisopropylphenylene.

The $C_7$-$C_{18}$-aralkylene is preferably tetramethylxylylene.

The alkyl radicals are preferably branched. In one embodiment of the invention the $C_3$-$C_{20}$-alkyl radicals here are linear and/or branched.

In the carbodiimides of the formula (I) according to the invention, the radicals $R^1$ to $R^6$ are preferably identical.

In another preferred embodiment of the invention the radicals $R^1$ to $R^6$ correspond to isopropyl.

The scope of the invention embraces all of the radical definitions, indices, parameters, and elucidations given above and set out below, whether general or in preference ranges, individually and among one another, hence including any desired combinations of the respective ranges and preference ranges.

The compounds of the formula (I) are thermally stable and are notable for outstanding activity as antihydrolysis agents/acid scavengers in ester group-containing polymers.

The present invention further provides a process for preparing the carbodiimides of the invention, whereby trisubstituted phenyl isocyanates of the formula (II)

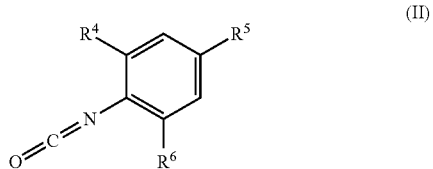

(II)

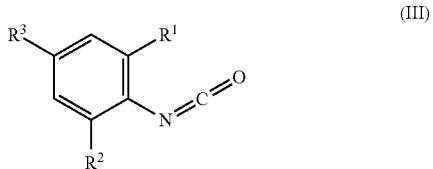

(III)

in which $R^1$, $R^2$, $R^3$, $R^4$, $R^5$, and $R^6$ independently of one another are each $C_1$-$C_{20}$-alkyl, $C_3$-$C_{20}$-cycloalkyl, $C_6$-$C_{15}$-aryl and/or $C_7$-$C_{15}$-aralkyl and compounds of the formula (IV)

(IV)

in which $R^7$ is $C_1$-$C_{18}$-alkylene, $C_5$-$C_{18}$-cycloalkylene, alkyl-substituted arylene, $C_7$-$C_{18}$-aralkylene, preferably alkyl-substituted arylene and/or $C_7$-$C_{18}$-aralkylene, and p represents integers 0-500, preferably 0-50, with p more preferably being ≥2, are carbodiimidized with elimination of carbon dioxide at temperatures of 40° C. to 200° C. in the presence of catalysts and optionally solvent.

The alkyl-substituted arylene is preferably $C_1$-$C_4$-alkyl-substituted arylene, more preferably singly to triply substituted $C_1$-$C_4$-alkyl-substituted arylene, very preferably triisopropylphenylene and/or tetramethylxylylene.

The trisubstituted phenyl isocyanates are preferably isocyanates such as 2,4,6-triisopropylphenyl isocyanate, 2,6-diisopropyl-4-tert-butylphenyl isocyanate, 2,6-diisopropyl-4-stearylphenyl isocyanate, 2,6-diisopropyl-4-dodecylphenyl isocyanate, 2,4,6-tri-tert-butylphenyl isocyanate, 2,4,6-tri-2-ethylhexylphenyl isocyanate, 2,6-diisopropyl-4-n-butylphenyl isocyanate, 2,4,6-tri-n-butylphenyl isocyanate, 2,4,6-tri-hexadecanylphenyl isocyanate and/or 2,4,6-trioctadecanylphenyl isocyanate.

The trisubstituted phenyl isocyanates can be prepared starting from trisubstituted anilines.

These trisubstituted anilines can be prepared—as the skilled person is aware—via a Friedel Crafts alkylation of aniline with the corresponding alkene, haloalkane, haloalkenebenzene and/or halocycloalkane. The diarylaniline derivatives may alternatively also be synthesized, for example, starting from the 2,6-dibromoaniline, by means of Suzuki coupling.

These trisubstituted anilines are subsequently reacted with phosgene to give the corresponding trisubstituted phenyl isocyanate. The trisubstituted anilines used are also available commercially, from Lonza Group Ltd., for example.

The compounds of the formula (IV) are commercial substances, which are available, for example, from Rhein Chemie Rheinau GmbH under the trade name Stabaxol® P 220 or Stabaxol® P 100, for example, or from Bayer MaterialScience AG, for example, under the trade name Desmodur® W, Desmodur® 1, Desmodur® 44 M, and Desmodur® T, for example.

The carbodiimidization here takes place preferably in accordance with the methods described in Angew. Chem. 93, pp. 855-866 (1981) or DE-A-11 30 594 or Tetrahedron Letters 48 (2007), pp. 6002-6004.

Preferred catalysts in one embodiment of the invention are strong bases or phosphorus compounds. Preference is given to using phospholene oxides, phospholidines, or phospholine oxides, and also the corresponding sulfides. As catalysts it is possible, furthermore, to use tertiary amines, basic metallic compounds, alkali metal or alkaline earth metal oxides or hydroxides, alkoxides or phenoxides, metal salts of carboxylic acids, and nonbasic organometallic compounds.

The carbodiimidization may be carried out both in bulk and in a solvent. In another embodiment of the invention the carbodiimidization is carried out first in bulk and subsequently in the solvent. Examples of solvents which can be used include benzines, benzene and/or alkylbenzenes.

The carbodiimides of the invention that are obtained may optionally be purified after the reaction. The crude products may be purified by means of recrystallization. Examples of suitable solvents that may be used for the recrystallization include alkylbenzenes, alcohols, ketones, ethers, or esters.

The present invention further provides for the use of the carbodiimides of the invention as stabilizer, crosslinker and/or compatibilizer in thermoplastics, such as polyethylene terephthalate (PET), polybutylene terephthalate (PBT), polytrimethylene terephthalate (PTT), in thermoplastic polyurethanes (TPU), copolyesters, such as the modified polyester formed from cyclohexanediol and terephthalic acid (PCTA), in thermoplastic polyester elastomers (TPEE), polylactic acid (PLA) and/or PLA derivatives, polyhydroxyalkanoates (PHA), starch-based plastics, polyamides (PA), such as polyamide 6, 6.6, 6.10, 6.12, 10, 11, 12, for example, or in blends, such as PA/PET blends or PHA/PLA blends, for example.

The invention further provides for the use of the carbodiimides of the invention as antihydrolysis agents in ester-based polyols, such as petrochemical or biobased polyols, for example, for rigid and flexible polyurethane foams, ester group-comprising polyurethane adhesives, lubricants and/or oils, such as in transformer oils, for example, and/or for polyurethane-based CASE (Coatings Adhesives Sealants Elastomers) applications.

The present invention further provides the use of the carbodiimides of the invention in solid form preferably for solids metering on continuously operating processing machines, such as single-screw, twin-screw, and multi-screw extruders, for example, continuously operating co-kneaders (Buss type), and discontinuously operating kneaders, of Banbury type, for example, and other assemblies customary in the polymer industry.

The present invention further provides the use of the carbodiimides of the invention in the production of polymeric films, more particularly PET films, TPU films, and PLA films.

The examples which follow serve to illustrate the invention, without having any limiting effect.

WORKING EXAMPLES

A carbodiimide based on tetramethylxylylene diisocyanate, reacted with polyethylene glycol monomethyl ether, obtainable under the name Stabaxol® P 200, and also a bis-2,6-diisopropylphenyl carbodiimide (Stabaxol® I) from Rhein Chemie Rheinau GmbH, was tested in comparison to the carbodiimide I of the invention, based on tetramethylxylylene diisocyanate, reacted with triisopropylphenyl isocyanate, and also a carbodiimide II, based on triisopropylphenyl diisocyanate and triisopropylphenyl isocyanate.

The aforementioned carbodiimides were tested in ester-based polymers for their antihydrolysis/acid number reduction effect.

Preparation of the Carbodiimides I and II of the Invention

A 500 ml flask with flat-ground joints, cleaned by baking and filled with nitrogen, was charged under a stream of nitrogen with 400 g of carbodiimide based on tetramethylxylylene diisocyanate (for carbodiimide I) or based on triisopropylphenyl diisocyanate (for carbodiimide II) and with 210 g of 2,4,6-triisopropylphenyl isocyanate, and this initial charge was heated to 140° C. Following addition of 400 mg of 1-methylphospholene oxide, the reaction mixture was heated to 180° C. over the course of 5 hours. This was followed by reaction at 180° C. until an NCO content of <1% had been reached.

Application Tests
Thermal Stability

For the determination of the thermal stability, thermogravimetric analyses were carried out with a TGA measuring apparatus from Mettler Toledo (TGA/SDTA851). In each case, 10-15 mg of sample were analyzed under nitrogen in a temperature ramp from 30 to 600° C. and at a heating rate of 10° C./min. An evaluation was made of the temperature in ° C. when a weight loss of 10% was reached.

Hydrolytic Stability of Polyethylene Terephthalate

To determine the hydrolytic stability, PET test specimens with 1.5% by weight of carbodiimide were investigated for tensile strength, following hydrolytic aging at 120° C. in saturated steam. An evaluation was made of the time in days taken for the tensile strength to reach a value of 0. As a further comparison, the PET not stabilized with carbodiimide was also tested.

The results are set out in Table 1:

TABLE 1

| Carbodiimide | TGA of carbodiimide [° C.] | Hydrolytic stability of PET [days] |
|---|---|---|
| No carbodiimide (C) | — | 2-3 |
| Stabaxol ® I (C) | 240 | 7 |
| Stabaxol ® P 200 (C) | 300 | 4-5 |
| CDI I (inv) | 300 | 7 |
| CDI II (inv) | 360 | 6-7 |

C = comparative example, inv = inventive

Test Results

The test results with the carbodiimides (I) and (II) of the invention show that in comparison to the carbodiimides known in the prior art, they exhibit very high activity as antihydrolysis agents/acid scavengers in ester-based polymers and/or in ester-based formulations, in conjunction with very good, or even improved, thermal stability.

What is claimed is:

1. A carbodiimide of the formula (I)

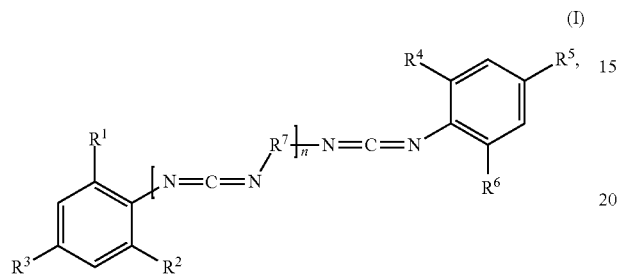

in which:
R$^1$, R$^2$, R$^3$, R$^4$, R$^5$, and R$^6$ independently of one another, are each C$_1$-C$_{20}$-alkyl, C$_3$-C$_{20}$-cycloalkyl, C$_6$-C$_{15}$-aryl, or C$_7$-C$_{15}$-aralkyl,
R$^7$ is C$_1$-C$_{18}$-alkylene, C$_5$-C$_{18}$-cycloalkylene, and/or C$_7$-C$_{18}$-aralkylene, and
n is an integer from 1 to 500.

2. The carbodiimide a claimed in claim 1, wherein the radicals R$^1$ to R$^6$ are identical.

3. The carbodiimide as claimed in claim 1 or 2, wherein the radicals R$^1$ to R$^6$ are isopropyl.

4. The carbodiimide as claimed in claim 1 or 2, wherein the C$_7$-C$_{18}$-aralkylene is tetramethylxylylene.

5. A process for preparing carbodiimides as claimed in claim 1, the process comprising carbodiimidizing:
trisubstituted phenyl isocyanates of the formula (II)

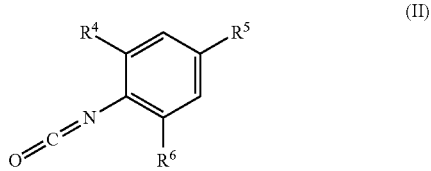

and of the formula (III)

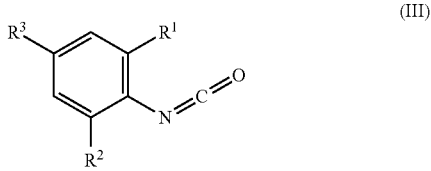

in which each R$^1$, R$^2$, R$^3$, R$^4$, R$^5$, and R$^6$, independently of one another, is C$_1$-C$_{20}$-alkyl, C$_3$-C$_{20}$-cycloalkyl, C$_6$-C$_{15}$-aryl or C$_7$-C$_{15}$-aralkyl, and
compounds of the formula (IV)

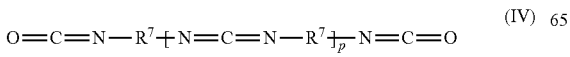

in which R$^7$ is C$_1$-C$_{18}$-alkylene, C$_5$-C$_{18}$-cycloalkylene, and/or C$_7$-C$_{18}$-aralkylene, and p represents integers 0-500,
with elimination of carbon dioxide at temperatures of 40 to 200° C. in the presence of a catalyst.

6. The carbodiimides as claimed in claim 1, wherein:
R$^7$ is C$_7$-C$_{18}$-aralkylene, and
n is an integer from 1 to 50.

7. The carbodiimides as claimed claim 6, wherein R$^7$ is tetramethylxylylene.

8. The carbodiimides as claimed in claim 6, wherein:
each of the radicals R$^1$ to R$^6$ within the molecule are isopropyl; and
n is an integer from 4-50.

9. A carbodiimide mixture comprising a plurality of different carbodiimides of the formula (I)

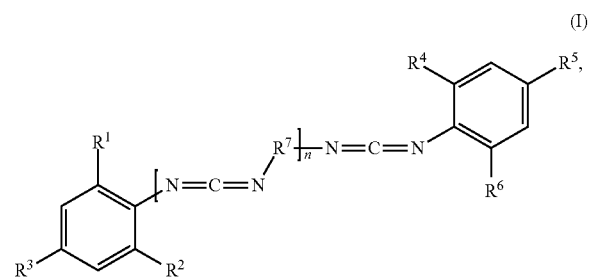

in which:
R$^1$, R$^2$, R$^3$, R$^4$, R$^5$, and R$^6$, independently of one another, are C$_1$-C$_{20}$-alkyl, C$_3$-C$_{20}$-cycloalkyl, C$_6$-C$_{15}$-aryl and/or C$_7$-C$_{15}$-aralkyl,
R$^7$ is C$_1$-C$_{18}$-alkylene, C$_5$-C$_{18}$-cycloalkylene, and/or C$_7$-C$_{18}$-aralkylene, and
n is an integer from 1 to 500.

10. The carbodiimides as claimed in claim 9, wherein:
n varies per carbodiimide molecule and is an integer from 4 to 50; and
the radicals R$^1$ to R$^6$ within each molecule are each isopropyl.

11. A carbodiimide composition comprising carbodiimides of the formula (I)

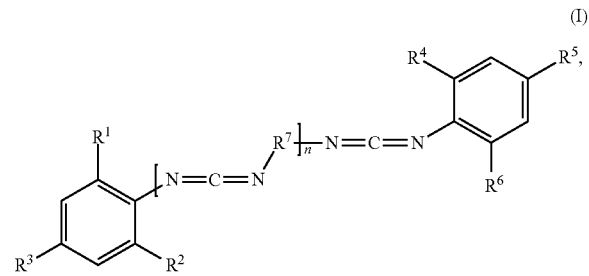

wherein the carbodiimides are the same or different carbodiimides of the formula (I) and in which:
R$^1$, R$^2$, R$^3$, R$^4$, R$^5$, and R$^6$, independently of one another, are each C$_1$-C$_{20}$-alkyl, C$_3$-C$_{20}$-cycloalkyl, C$_6$-C$_{15}$-aryl, or C$_7$-C$_{15}$-aralkyl,
R$^7$ is C$_1$-C$_{18}$-alkylene, C$_5$-C$_{18}$-cycloalkylene, alkyl-substituted arylene and/or C$_7$-C$_{18}$-aralkylene, and
n is an integer from 4 to 500.

12. The carbodiimides as claimed in claim 11, wherein $R^7$ is singly to triply substituted $C_1$-$C_4$-alkyl-substituted arylene.

13. The carbodiimides as claimed claim 6, wherein $R^7$ is triisopropylphenylene.

14. The carbodiimides as claimed in claim 13, wherein the carbodiimides are the same and the radicals $R^1$ to $R^6$ are isopropyl.

* * * * *